United States Patent [19]

Lamont et al.

[11] 4,101,422
[45] Jul. 18, 1978

[54] COPOLYESTERS USEFUL IN BLOOD SEPARATION ASSEMBLIES

[75] Inventors: James Lamont; Robert J. Braun, both of Cincinnati, Ohio

[73] Assignee: Emery Industries, Inc., Cincinnati, Ohio

[21] Appl. No.: 795,992

[22] Filed: May 11, 1977

[51] Int. Cl.² .............................................. B01D 21/26
[52] U.S. Cl. ................................... 210/84; 23/230 B; 23/258.5 R; 23/259; 128/2 F; 128/2 G; 233/1 A; 210/515; 210/516; 210/518
[58] Field of Search ................. 233/1 A, 26; 128/2 F, 128/2 G; 23/230 B, 258.5 R, 259; 106/287 R, 162; 260/31.6, 31.8 R, 31.8 XA, 37 R, 40 R, 860, 45.85 R; 252/60, 62.3 Q, 259.5; 210/83, 84, 78, 513–516, 518, DIG. 23

[56] References Cited
U.S. PATENT DOCUMENTS 3,852,194  12/1974  Zine ............................ 210/DIG. 23

Primary Examiner—Frank Sever
Attorney, Agent, or Firm—Gerald A. Baracka; John D. Rice

[57] ABSTRACT

Copolyesters are provided which are derived from mixed dibasic acids and a branched-chain diol. These copolyesters possess a unique balance of physical and chemical characteristics which permits their use in small amounts in blood separation tubes to provide an effective barrier between the light and heavy phases of the blood after centrifuging.

4 Claims, No Drawings

COPOLYESTERS USEFUL IN BLOOD SEPARATION ASSEMBLIES

BACKGROUND OF THE INVENTION

Much effort has been directed to the development of assemblies for separating blood serum or plasma from the cellular portion of the blood. To accomplish this separation the assembly, typically an elongated glass cylinder of varying design and containing the blood sample, is subjected to ultracentrifugation until the cellular portion (heavy phase) and serum or plasma (light phase) are completely separated. To maintain separation after centrifuging and to facilitate decanting or removal of the light phase by pipette a barrier means is provided within the assembly between the phases.

Numerous sealing devices manufactured from elastomeric materials have been proposed as barriers. To illustrate just a few, reference may be had to the following U.S. Pat. Nos. 3,779,383; 3,891,553; 3,894,951; 3,897,337; 3,897,340, 3,897,343, 3,931,010; and 3,957,654. Also, U.S. Pat. No. 3,919,085 describes an elastomeric barrier which is in a deformed condition prior to separation but after centrifuging assumes a sealing configuration at the interface of the two phases. The use of encapsulated beads to establish a seal between a pair of slideable cylinders is described in U.S. Pat. No. 3,909,419. Beads or granules having the proper specific gravity and coated with an adhesive material, such as a silicone fluid, are described as barriers in U.S. Pat. No. 3,920,557. U.S. Pat. No. 3,972,812 describes the use of porous discs made of a polymeric material, such as sintered nylon, styrene, polyethylene or polypropylene, and sprayed with a hydrophobic material.

The current trend is away from the use of manufactured sealing devices requiring extremely close tolerances and which are costly and difficult to manufacture. Recent emphasis has been toward the development of liquid sealant materials which are inserted directly into the assembly before or after collection of the blood sample and which accomplish the same result. For example, the separation of a sample of blood into the serum and clot portions is accomplished using a sealant (barrier) consisting of a silicone fluid having silica dispersed therein as shown in U.S. Pat. No. 3,780,935. U.S. Pat. No. 4,018,564 describes a method for analyzing a blood sample by the addition, prior to centrifuging, of a small but effective amount of a three-component blood separating composition comprising a diorganopolysiloxane, a silica filler and polyether stabilizer. Such barrier compositions, in addition to being inert and having the proper density to enable them to locate between the two phases, are highly viscous, homogeneous, hydrophobic materials. By homogeneous is meant that the materials themselves will not separate into two or more phases upon ultracentrifugation.

It would be highly advantageous if lower cost polymeric materials, such as polyesters, could be advantageously employed in such applications. Both terminated and non-terminated polyesters and copolyesters derived from a variety of polyols and polybasic acids and having molecular weights from about 500 to 50,000 or higher are known. It is also known to employ mixtures of polyols and polybasic acids to obtain useful products. U.S. Pat. Nos. 3,055,869 and 3,194,791, for example, disclose processes for preparing polyesters from a wide variety of dicarboxylic acids and dihydroxy compounds with an optional chain-terminating monobasic acid or monohydric alcohol. U.S. Pat. No. 3,057,824 also teaches that mixed polycarboxylic acids and mixtures of diols can be esterified for the preparation of polyesters having high hydroxyl values which are useful for the preparation of polyurethane coatings and foams. Polymeric fatty acids are disclosed as suitable dicarboxylic acids in these and in other references such as U.S. Pat. No. 2,429,219 where superpolyesters having molecular weights greater than 10,000 are obtained by reacting dimer acid and linear aliphatic glycols. Adipic acid is also employed with the dimer acid for the preparation of one of the superpolyesters. U.S. Pat. No. 2,384,443 also describes rubber-like compositions obtained by reacting a polymeric fatty acid and straight-chain aliphatic glycols. Mixtures of dimer and aromatic dicarboxylic acids have been reacted with polymethylene glycols as shown in U.S. Pat. Nos. 3,235,520 and 3,383,343.

SUMMARY OF THE INVENTION

We have now quite unexpectedly discovered novel high molecular weight copolyesters which satisfy all of the above requirements and which are derived from a short-chain dibasic acid, a polymeric fatty acid and a branched-chain saturated aliphatic diol or a mixture of diols having a branched-chain diol as the principal component. These copolyester compositions are advantageously employed in small amounts in blood separation tubes and form a tight seal between the light and heavy phases of the blood. The polyester compositions are not affected by contact with the blood and they do not alter the blood components. They are highly viscous copolyester products and have a density so that during the ultracentrifugation they locate at the interface between the serum or plasma phase and heavier cellular phase and when the centrifuging is terminated form a continuous integral barrier within the assembly to prevent the phases from recombining or mixing especially when decanting or pipetting the light phase. A small but effective amount, generally 2 to 5 grams, of the copolyester sufficient to form the barrier between the phases is inserted directly into the separation tube either before or after the blood sample is collected.

The copolyesters are broadly characterized as being inert, hydrophobic, homogeneous compositions having molecular weights from about 2,000 to 8,000, densities in the range 1.015 to 1.060 g/cm$^3$ and 210° F viscosities (kinematic) in the range 2,000 to 8,000 centistokes. Preferably, these copolyesters will have a molecular weight from 3,000 to 6,000 and density between about 1.020 and 1.050 g/cm$^3$. They are obtained by the reaction of essentially stoichiometric amounts of a mixture of a saturated aliphatic dicarboxylic acid having 4 to 12, and preferably 6 to 10, carbon atoms and a polymeric fatty acid containing 75% by weight or more C$_{36}$ dimer acid with a branched-chain aliphatic dihydric alcohol having 3 to 8, and more preferably 3 to 5, carbon atoms. The equivalents ratio of short-chain acid to polymer acid ranges from 0.80:0.20 to 0.97:0.03. Especially useful copolyesters are derived from polymeric fatty acids having 85% by weight or more C$_{36}$ dimer, adipic, azelaic or sebacic acids and neopentyl glycol or a mixture or neopentyl glycol and 1,2-propanediol. The copolyesters can be combined with up to 35 weight percent of an inert filler such as silica.

DETAILED DESCRIPTION

This invention relates to high molecular weight copolyesters derived from specific mixed dibasic acids and a branched-chain aliphatic diol or mixture of such diols. When these reactants are combined in the prescribed ratios and esterified using conventional esterification techniques copolyesters having molecular weights from about 2,000 to 8,000 which are effective blood-separating compositions are obtained. The highly viscous copolyester compositions of this invention preferably have molecular weights in the range 3,000 to 6,000. They are inert, hydrophobic, i.e., exhibit negligible water solubility, polymers which do not undergo phase separation when subjected to ultracentrifugation even for prolonged periods. Typically, these homogeneous copolyesters can withstand up to four hours ultracentrifugation at up to 250,000 G (G is the ratio of centrifugal acceleration to acceleration of gravity) without any detectable phase separation. The compostions of this invention have 210° F viscosities (kinematic) in the range 2,000 to 8,000 centistokes and a density in the range 1.015 and 1.060 g/cm$^3$. More preferably they have a 210° F kinematic viscosity in the range 3,000 to 6,000 and density in the range 1.020 to 1.050 g/cm$^3$.

Copolyesters having the above-defined properties are highly useful in blood separation assemblies and provide a continuous integral barrier or seal between the serum and clot portions of blood. By continuous is meant that the copolyester completely separates the phases so that the serum and clot portions are no longer in contact at any point. By integral is meant that the copolyester forms a tight seal against the inner surface of the blood separation assembly. By forming a continuous integral barrier it is then possible to easily remove the serum portion by decanting or pipetting and the clot portion is retained undisturbed in the assembly.

To obtain copolyesters having the aforementioned characteristics, which as a result of their unique physical and chemical properties are useful compositions for use in blood separation assemblies to form an effective barrier between the serum or plasma phase and the heavier cellular (clot) phase, as specific reactant mix is necessary. The useful copolyesters of this invention are formed by the reaction of a mixture of dibasic acids consisting of a short-chain dibasic acid and a polymeric fatty acid with a branched-chain saturated aliphatic diol.

Short-chain dibasic acids useful for the preparation of the copolyesters are saturated aliphatic dicarboxylic acids having 4 to 12 carbon atoms. More preferably, these acids will have from 6 to 10 carbon atoms and are essentially straight-chain acids. Illustrative dicarboxylic acids include glutaric acid, adipic acid, pimelic acid, suberic acid, azelaic acid, sebacic acid, undecanedioic acid and dodecanedioic acid. Mixtures of two or more of these short-chain dibasic acids can also be used. Particularly useful copolyester compositions are obtained when adipic acid, azelaic or sebacic acid is employed with the polymeric fatty acid.

The polymeric fatty acids are obtained by the polymerization of olefinically unsaturated monocarboxylic acids having from 16 to 20 carbon atoms, such as oleic acid, linolenic acid, linoleic acid, eleostearic acid and the like. Polymeric fatty acids and processes for their production are known to the art and by way of illustration reference may 190-215 had to U.S. Pat. Nos. 2,793,219 and 2,955,121. Polymer fatty acids useful for this invention preferably will have as their principal component $C_{36}$ dimer acid. $C_{36}$ dibasic acids are obtained by the dimerization of two moles of a $C_{18}$ unsaturated monocarboxylic acid such as oleic acid or linoleic acid or mixtures thereof (e.g. tall oil fatty acids). They typically contain 75% by weight or more $C_{36}$ dimer acid and have an acid value in the range 180–215, saponification value in the range 190-215 and neutral equivalent from 265 to 310. The dimer acids may be hydrogenated prior to use. To increase the $C_{36}$ dimer content and reduce the amount of by-product acids including unreacted monobasic acid, trimer and higher polymer acids, the polymeric fatty acid can be molecularly distilled or otherwise fractionated. Especially useful copolyester compositions are obtained using polymeric fatty acids having $C_{36}$ dibasic acid contents of 85% by weight or more.

The equivalents ratio of short-chain dibasic acid to polymeric fatty acid will range from about 0.80:0.20 to 0.97:0.03 and more preferably will be in the range 0.85:0.15 to 0.95:0.05. An essentially stoichiometric amount of the dibasic acid mixture is reacted with the branched-chain diol(s) to obtain the copolyesters.

To obtain the highly useful copolyesters of this invention it is necessary that a branched-chain aliphatic dihydric aclohol having 3 to 8 carbon atoms be reacted with the dibasic acid mixture. Mixtures of branched-chain diols are also advantageously employed as are mixtures of a branched-chain and straight-chain aliphatic saturated diols wherein the branched-chain diol constitutes at least 50 percent by weight, and more preferably, greater than 70 percent by weight of the total diols present. The hydroxyl groups of the diol may be either primary or secondary, however, diols having tertiary hydroxyl groups are not recommended. For the purpose of this invention a diol containing a secondary hydroxyl group is considered to be a branched-chain diol. Useful branched-chain diols include 2,2-dimethyl-1,3-propanediol (neopentyl glycol), 2-methyl-1,3-propanediol, 3-methyl-1,5-pentanediol, 2,2,4-trimethyl-1,3-pentanediol, 3-methyl-2,3-pentanediol, 1,2-propanediol, 1,3-butanediol, 1,2-butanediol, 1,2-pentanediol, 1,3-pentanediol, 1,4-pentanediol and the like. Preferred diols for this invention contain from 3 to 5 carbon atoms and exceptional results are obtained using neopentyl glycol or a mixture of neopentyl glycol and 1,2-propanediol. In one of the preferred embodiments of this invention where a mixture of neopentyl glycol and 1,2-propanediol is used the equivalents ratio of the respective diols ranges from 0.85:0.15 to 0.99:0.01. Useful straight-chain (linear) aliphatic diols can have from 2 to 8 carbon atoms and include, for example, ethylene glycol, 1,3-propanediol, 1,4-butanediol, 1,6-hexanediol and the like.

Conventional esterificatin procedures and equipment are used to obtain the copolyesters. The reactants are usually added to the esterification kettle as a unit charge and the mixture is then heated with agitation at a temperature from about 150° C to 250° C. When the reaction rate slows a vacuum is generaly applied to the system to drive the reaction.

The rate of esterification can be enhanced by the use of known esterification catalysts. If a catalyst is used it is not necessary that it be present throughout the entire reaction. It is sometimes advantageous in order to obtain products having good color and low acid value, preferably less than 10, to add the catalyst during the final stages of the reaction. At the same time the pressure can be reduced for even better results. While the esterification can be carried out entirely at atmospheric pressure it is most desirable to reduce the pressure, typically to about 1–50 mm Hg. at 200°–250° C), during the latter stages to facilitate removal of the final traces of water and excess glycol which may be present and to reduce the acid value to the desired level. Suitable esterification catalysts include phosphoric acid, sulfuric acid, p-toluenesulfonic acid, methanesulfonic acid, stannous oxalate, alkyl tin oxides, tetrabutyl titanate, zinc acetate, sodium carbonate and the like. The amount and type of catalyst can vary widely but it will most often be present in an amount from about 0.01% to about 0.5% by weight based on the total reactant charge. At the completion of the reaction the catalyst can be deactivated and removed by filtering or other conventional means.

Inert diluents such as benzene, toluene, xylene and the like can be used to carry out the reaction but they are not necessary and the reaction is generally conducted without such diluents since in this way the copolyesters can be used directly as obtained from the reactor without the need for stripping. As indicated above all of the reactants are usually charged to the reactor at the outset, however, the method of charging can be varied depending on the equipment used. It will be evident to one skilled in the art that if the esterification is carried out in a continuous or semi-continuous manner it will be necessary to replenish the reactants as they are consumed. Multiple vessel arrangements can be used for continuous production of these copolyesters.

A small excess (based on the equivalents of acids present) of the diol component can be used. The excess diol serves as the reaction medium and reduces the viscosity of the reaction mixture. The excess glycol is distilled off as the esterification is carried to completion and can be recycled to the reactor is desired. Generally, about 20% by weight excess diol will suffice and the more volatile glycols are commonly used for this purpose. It is not necessary that the excess diol be a branched-chain diol of the type required to obtain the defined copolyesters but 1,2-propanediol is advantageously used and preferred for this purpose.

The copolyesters of this invention can be combined with up to about 35 weight percent of an inert filler. These fillers can be added to the copolyester to increase the density of the copolyester composition since all of the commonly used fillers have densities greater than that of the copolyester. The fillers also impart thixotropic properties to the barrier compositions. Copolyesters containing small amounts of inert fillers, particularly silica, exhibit improved flow characteristics during centrifuging so that the compositions more readily locate at the interface between the light and heavy phases. When centrifuging is terminated, however, the compositions return to their original state and form a highly viscous, continuous and integral barrier between the clot and serum portions. The inert fillers used are in a finely powdered state and preferably constitute from about 0.5 to 25 weight percent of the total composition. While silica, including the various amorphous forms of silica, such as precipitated silica and fumed silica, and the hydrophobic silicas treated with silanes or polysiloxanes, are particularly useful with the copolyesters of this invention other inert materials such as alumina, talc and other silicates, bentonite and other naturally occurring montmorillonite-rich mineral clays can also be employed.

The following examples illustrate the invention more fully, however, they are not intended as a limitation on the scope thereof. In the examples all parts and percentages are on a weight basis unless otherwise indicated.

EXAMPLE I

To demonstrate the preparation of typical copolyester compositions of this invention the following esterification was conducted. The reaction was carried out in a four-necked, round-bottom flask equipped with a stirrer, thermometer, nitrogen inlet tube and a medium length Vigreaux column fitted with a condenser, distillation head with thermometer and receiver. The condenser was arranged so that water and/or excess diol could be distilled from the reaction mixture at either atmospheric or reduced pressure. The reactant charge was as follows:

|  | Parts |
| --- | --- |
| Azelaic Acid | 1588 |
| Dimer Acid* | 531 |
| Neopentyl Glycol | 869 |
| 1,2-Propanediol | 211 |

*Empol ® 1016 containing 87% $C_{36}$ dibasic acid.

The equivalents ratio of the above charge (azelaic:dimer:neopentyl glycol: 1,2-propanediol) is 0.90:0.10:0.90:0.10. About 15 weight percent excess of the 1,2-propanediol was added. The temprature of the reaction mixture was brought to about 225° C while maintaining the vapor temperature at about 100°–120° C and removing water of reaction. After about four hours when the rate of water evolution slowed and the vapor temperature dropped below 100° C, a vacuum (11 mm Hg.) was applied to the system to maintain the vapor temperature at 100° C or slightly above. Samples were taken from the reaction mixture at regular intervals to determine the acid value in accordance with AOCS Method Te 1a-64 T. After about 8 hours the acid value was 12.9. A small amount (0.03 wt. percent based on the total reactant charge) of a tin esterification catalyst was then added and the pressure reduced to about 4.5 mm Hg. After about 6 hours additional reaction time the acid value was less than 1 and the highly viscous reaction mixture was discharged from the reactor and allowed to cool. The copolyester, obtained in 99% yield, had an acid value of 0.2, hydroxyl value (AOCS Method Cd 13-60) of 13.0, molecular weight of 4334 (determined in benzene by vapor phase osmometry), 210° F kinematic viscosity of 4316 centistokes and 320° F kinematic viscosity of 839 centistokes. The clear, light-colored product had a density of 1.027 g/cm$^3$, was insoluble in water and showed no detectable phase separation after four hours ultracentrifugation at 250,000 G. 2–5 Grams of this copolyester provide an effective barrier between the serum and clot portions of a blood sample in a cylindrical collection tube (diameter 1.3 cm) upon ultra-centrifugation. The copolyester forms a tight seal with the inner surface of the glass cylinder so that the serum portion is easily decanted from the clot portion which is retained undisturbed behind the barrier.

The density of the copolyester can be adjusted and the flow properties altered by the addition of a small amount of an inert silica filler. Finely powdered silica is readily dispersed in the copolyester at levels up to about 25 weight percent. Thixotropic characteristics are imparted to the copolyester by the addition of this small particle size amorphous silica. This thixotropic character facilitates location of the copolyester composition at the interface between the phases during centrifugation but when centrifuging is completed the composition returns to its highly viscous original state.

EXAMPLE II

A copolyester was prepared in the same manner as described in Example I using identical reactants and reactant charges. The total reaction time was only 11 hours. A vacuum of 1.5 mm Hg. was applied during the final 3 hours of the reaction. The resulting copolyester product (98.4% yield) had an acid value of 1.0, 210° F kinematic viscosity of 6792 centistokes and density of 1.029 g/cm$^3$. This product is also an effective barrier composition for use in blood separation assemblies particularly when combined with about 15 weight percent small particle size fumed silica. Similar useful copolyester compositions are obtained when ethylene glycol or 1,3-propanediol is substituted for the 1,2-propanediol and when sebacic acid is substituted for azelaic acid.

EXAMPLES III – VII

To demonstrate the ability to vary the compositions of the copolyesters the equivalents ratio of azelaic acid and dimer acid was varied. For these examples the reaction conditions and the ratio of equivalents of neopentyl glycol and 1,2-propanediol were the same as employed in Example I. The table below lists the equivalents ratio of azelaic acid and dimer acid as well as the acid value, 210° F kinematic viscosity and density of the resulting copolyesters.

| Example No. | Equivalents Ratio (azelaic:dimer) | Acid Value | 210° F Viscosity (centistokes) | Density (g/cm$^3$) |
|---|---|---|---|---|
| III | 0.885:0.115 | 0.5 | 2755 | 1.023 |
| IV | 0.88:0.12 | 0.7 | 2918 | 1.022 |
| V | 0.89:0.11 | 1.0 | 4767 | 1.024 |
| VI | 0.93:0.07 | 0.5 | 3922 | 1.033 |
| VII | 0.97:0.03 | 0.8 | 3484 | 1.043 |

All of the copolyester products were homogeneous compositions exhibiting a high degree of hydrophobicity and were essentially chemically inert with respect to the blood components. They all are effective barrier materials for separating the serum portion and the clot portion of blood samples.

EXAMPLE VIII

In a manner similar to that described in Example I, a copolyester was prepared by the esterification of a mixture of adipic acid and dimer acid with a mixture of neopentyl glycol and 1,2-propanediol. The equivalents ratio of adipic acid to dimer acid was 0.511:0.063 and the equivalents ratio of neopentyl glycol to 1,2-propanediol was 0.517:0.057. 15 Percent excess of the 1,2-propanediol was used for the reaction and 0.01% $H_3PO_2$ was also added at the outset of the reaction. When the acid value of the reaction mixture was about 15 (approx. 5 hours) 0.03% of an organotin catalyst was added. The pressure was reduced to 1 mm Hg. during the final 4 hours of reaction. The copolyester (color of 4 on the Gardner scale) had a final acid value of 0.6 with a 210° F viscosity of 3815 centistokes. The density of the copolyester composition was 1.058 g/cm$^3$.

EXAMPLE IX

A copolyester composition was obtained by reacting azelaic acid, dimer acid containing 87 weight percent $C_{36}$ dimer and 1,3-butanediol at an equivalents ratio of 0.511:0.063:0.574. A slight excess of the 1,3-butanediol containing a small amount of $H_3PO_2$ was added to facilitate the reaction. After about eight hours when the acid value was less than 20 a vacuum was applied to the system and a small amount of tin esterification catalyst added. The vacuum was reduced to 1 mm Hg. during the final 2 hours of reaction. The final copolyester product had an acid value of 2.8, hydroxyl value of 9.5, 210° F viscosity of 3150 centistokes and density of 1.028 g/cm$^3$. Similar results are obtained using dimer acids containing about 80% $C_{36}$ dimer and greater than 95% $C_{36}$ dimer and when 1,2-propanediol or 1,3-propanediol was included with the 1,3-butanediol.

EXAMPLE X

672 Parts azelaic acid, 250 parts dimer acid containing about 85 weight percent $C_{36}$ dibasic acid and 378 parts 1,2-propanediol (equivalents ratio of the respective components 0.511: 0.063: 0.575) were reacted in the usual manner to an acid value of 0.8. The copolyester, obtained in 84% yield, and useful as a barrier material in blood separation assemblies had a 210° F viscosity of 5159 centistokes and density of 1.041 g/cm$^3$.

We claim:

1. A method of separating the serum and clot portions of a blood sample which comprises centrifuging the blood in a blood separation assembly with a small but effective amount of an inert, homogeneous, hydrophobic copolyester having a 210° F viscosity of 2,000 to 8,000 centistokes, density in the range 1.015 to 1.060 g/cm$^3$ and obtained by the reaction of essentially stoichiometric amounts of
   (a) a saturated aliphatic dicarboxylic acid having 4 to 12 carbon atoms,
   (b) a polymeric fatty acid containing 75% by weight or more $C_{36}$ dibasic acid, and
   (c) a branched-chain aliphatic dihydric alcohol having 3 to 8 carbon atoms, a mixture of said branched-chain dihydric alcohols, or a mixture containing at least 50% by weight said branched-chain aliphatic dihydric alcohols and a straight-chain aliphatic dihydric alcohol having 2 to 8 carbon atoms, the equivalents ratio of (a) to (b) ranging from 0.80:0.20 to 0.97:0.03, until the copolyester locates at the interface between the serum and clot portions and forms a continuous integral barrier therebetween.

2. The method of claim 1 wherein the copolyester has a density of 1.020 and 1.050 g/cm$^3$ and contains up to about 35 weight percent of an inert filler selected from the group consisting of alumina, silica, talc and bentonite.

3. The method of claim 2 wherein the copolyester is derived from a saturated aliphatic dicarboxylic acid having from 6 to 12 carbon atoms, a polymeric fatty acid containing 85% or more $C_{36}$ dibasic acid and a mixture of neopentyl glycol and 1,2-propanediol present in an equivalents ratio of 0.85:0.15 to 0.99:0.01.

4. The method of claim 3 wherein the copolyester contains 5 to 25 weight percent silica.

* * * * *